(12) United States Patent
Yang et al.

(10) Patent No.: US 9,249,122 B1
(45) Date of Patent: Feb. 2, 2016

(54) PROCESS FOR THE PREPARATION OF 3-(3-CHLORO-1H-PYRAZOL-1-YL)PYRIDINE

(71) Applicant: Dow AgroSciences LLC, Indianapolis, IN (US)

(72) Inventors: Qiang Yang, Zionsville, IN (US); Beth Lorsbach, Indianapolis, IN (US); Xiaoyong Li, Midland, MI (US); Gary Roth, Midland, MI (US); David E. Podhorez, Midland, MI (US)

( * ) Notice: Subject to any disclaimer, the term of this patent is extended or adjusted under 35 U.S.C. 154(b) by 0 days.

(21) Appl. No.: 14/517,315

(22) Filed: Oct. 17, 2014

Related U.S. Application Data

(60) Provisional application No. 62/031,547, filed on Jul. 31, 2014.

(51) Int. Cl.
| | | |
|---|---|---|
| C07D 401/04 | (2006.01) | |
| C07D 231/14 | (2006.01) | |
| C07D 403/04 | (2006.01) | |
| A01N 43/46 | (2006.01) | |
| A61K 31/415 | (2006.01) | |

(52) U.S. Cl.
CPC .................................. C07D 401/04 (2013.01)

(58) Field of Classification Search
CPC .... C07D 231/14; C07D 403/04; A01N 43/46; A61K 31/415
USPC .............. 514/352, 406; 546/275.4; 548/364.1
See application file for complete search history.

(56) References Cited

U.S. PATENT DOCUMENTS

| | | | |
|---|---|---|---|
| 3,597,341 | A | 9/1968 | Alexis |
| 4,080,457 | A | 3/1978 | Harrison et al. |
| 4,260,765 | A | 4/1981 | Harrison et al. |
| 4,407,803 | A | 10/1983 | Haviv et al. |
| 4,536,506 | A | 8/1985 | Marcoux et al. |
| 4,824,953 | A | 4/1989 | Bronn |
| 5,220,028 | A | 6/1993 | Iwasawa et al. |
| 5,625,074 | A | 4/1997 | Daum et al. |
| 5,631,380 | A | 5/1997 | Haas et al. |
| 5,652,372 | A | 7/1997 | Muller et al. |
| 5,693,657 | A | 12/1997 | Lee et al. |
| 5,750,718 | A | 5/1998 | Muller et al. |
| 5,817,677 | A | 10/1998 | Linz et al. |
| 5,854,264 | A | 12/1998 | Anthony et al. |
| 5,854,265 | A | 12/1998 | Anthony et al. |
| 5,869,681 | A | 2/1999 | Muller et al. |
| 6,040,331 | A | 3/2000 | Yamamoto et al. |
| 6,218,418 | B1 | 4/2001 | Pevarello et al. |
| 6,506,747 | B1 | 1/2003 | Betageri et al. |
| 6,548,525 | B2 | 4/2003 | Galemmo, Jr. et al. |
| 6,720,427 | B2 | 4/2004 | Sanner et al. |
| 6,878,196 | B2 | 4/2005 | Harada et al. |
| 6,916,927 | B2 | 7/2005 | Bunnage et al. |
| 6,965,032 | B2 | 11/2005 | Freudenberger et al. |
| 7,192,906 | B2 | 3/2007 | Hirohara et al. |
| 7,196,104 | B2 | 3/2007 | Askew, Jr. et al. |
| 7,319,108 | B2 | 1/2008 | Schwink et al. |
| 7,774,978 | B2 | 8/2010 | Ding et al. |
| 7,803,832 | B2 | 9/2010 | Critcher et al. |
| 7,910,606 | B2 | 3/2011 | Nazare et al. |
| 7,923,573 | B2 | 4/2011 | Tamaki et al. |
| 8,163,756 | B2 | 4/2012 | Flynn et al. |
| 8,222,280 | B2 | 7/2012 | Liu et al. |
| 8,901,153 | B2 | 12/2014 | Buysse et al. |
| 2002/0013326 | A1 | 1/2002 | Tiebes et al. |
| 2003/0153464 | A1 | 8/2003 | Nakamura et al. |
| 2003/0213405 | A1 | 11/2003 | Harada et al. |
| 2004/0043904 | A1 | 3/2004 | Yamaguchi et al. |
| 2004/0082629 | A1 | 4/2004 | Iwataki et al. |
| 2005/0038059 | A1 | 2/2005 | Mueller et al. |
| 2005/0176710 | A1 | 8/2005 | Schwink et al. |
| 2006/0135778 | A1 | 6/2006 | Schnatterer et al. |
| 2006/0160857 | A1 | 7/2006 | Buettelmann et al. |
| 2006/0160875 | A1 | 7/2006 | Gaines et al. |
| 2006/0167020 | A1 | 7/2006 | Dickerson et al. |
| 2006/0287365 | A1 | 12/2006 | Billen et al. |
| 2006/0287541 | A1 | 12/2006 | Nishino et al. |
| 2007/0049604 | A1 | 3/2007 | Nam et al. |
| 2007/0167426 | A1 | 7/2007 | Siddiqui et al. |
| 2008/0004301 | A1 | 1/2008 | Tamaki et al. |
| 2008/0027046 | A1 | 1/2008 | Annan et al. |
| 2009/0023709 | A1 | 1/2009 | Gillespie et al. |

(Continued)

FOREIGN PATENT DOCUMENTS

| | | |
|---|---|---|
| EP | 0097323 A2 | 1/1984 |
| EP | 0190457 A1 | 8/1986 |

(Continued)

OTHER PUBLICATIONS

Kempe et al. 'Responsive Glyco-poly(2-oxazoline)s: Synthesis, Cloud Point Tuning, and Lectin Binding,' Biomacromolecules 2011, vol. 12, pp. 2591-2600.

Fields et al. 'Preparation of Trifluoromethyl-Pyrazoles and -Pyrazolines by the Reaction of 2,2,2-Trifluorodiazoethane With Carbon—Carbon Multiple Bonds,' Journal of Fluorine Chemistry, 1979, vol. 13, pp. 147-158.

Bradbury et al. 'Enzyme-catalysed peptide amidation,' Eur. J. Biochem. 1987, vol. 169, pp. 579-584.

International Search Report and Written Opinion for PCT/US2014/061005 mailed Dec. 16, 2014.

International Search Report and Written Opinion for PCT/US2014/061006 mailed Dec. 8, 2014.

(Continued)

Primary Examiner — John Mabry
Assistant Examiner — Daniel Carcanague
(74) Attorney, Agent, or Firm — Barnes & Thornburg LLP; Carl Corvin

(57) ABSTRACT

3-(3-Chloro-1H-pyrazol-1-yl)pyridine is prepared by cyclizing 3-hydrazinopyridine•dihydrochloride with acrylonitrile to provide 1-(pyridin-3-yl)-4,5-dihydro-1H-pyrazol-3-amine, by oxidizing to provide 3-(3-amino-1H-pyrazol-1-yl) pyridine, and by converting the amino group to a chloro group by a Sandmeyer reaction.

4 Claims, No Drawings

(56) References Cited

U.S. PATENT DOCUMENTS

| | | |
|---|---|---|
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |

FOREIGN PATENT DOCUMENTS

| | | |
|---|---|---|
| EP | 0205024 A2 | 12/1986 |
| EP | 0248315 A2 | 12/1987 |
| EP | 0425948 A2 | 5/1991 |
| EP | 1273582 A1 | 1/2003 |
| EP | 1321463 A1 | 6/2003 |
| EP | 1329160 A2 | 7/2003 |
| JP | 1987-153273 A | 7/1987 |
| JP | 1988-174905 A | 7/1988 |
| JP | 1989-226815 A | 9/1989 |
| JP | 2003-212864 A | 7/2003 |
| JP | 2004-051628 A | 2/2004 |
| JP | 2004-292703 A | 10/2004 |
| JP | 2012-188418 A | 10/2012 |
| JP | 2013-075871 A | 4/2013 |
| JP | 2013-082699 A | 5/2013 |
| JP | 2013-082704 A | 5/2013 |
| JP | 2013-107867 A | 6/2013 |
| JP | 2013-129651 A | 7/2013 |
| JP | 2013-129653 A | 7/2013 |
| WO | WO 94/13644 A1 | 6/1994 |
| WO | WO 97/36897 A1 | 10/1997 |
| WO | WO 98/49166 A1 | 11/1998 |
| WO | WO 00/35919 A2 | 6/2000 |
| WO | WO 01/34127 A1 | 5/2001 |
| WO | WO 01/90078 A1 | 11/2001 |
| WO | WO 02/083111 A2 | 10/2002 |
| WO | WO 03/008405 A1 | 1/2003 |
| WO | WO 03/072102 A1 | 9/2003 |
| WO | WO 2004/041813 A1 | 5/2004 |
| WO | WO 2005/070925 A1 | 8/2005 |
| WO | WO 2005/074875 A2 | 8/2005 |
| WO | WO 2006/023462 A1 | 3/2006 |
| WO | WO 2006/033005 A2 | 3/2006 |
| WO | WO 2006/046593 A1 | 5/2006 |
| WO | WO 2006/103045 A1 | 10/2006 |
| WO | WO 2007/005838 A2 | 1/2007 |
| WO | WO 2007/087427 A2 | 8/2007 |
| WO | WO 2007/098826 A2 | 9/2007 |
| WO | WO 2008/005457 A2 | 1/2008 |
| WO | WO 2008/079277 A1 | 7/2008 |
| WO | WO 2008/090382 A1 | 7/2008 |
| WO | WO 2009/149858 A1 | 12/2009 |
| WO | WO 2010/006713 A2 | 1/2010 |
| WO | WO 2010/009290 A1 | 1/2010 |
| WO | WO 2010/012442 A2 | 2/2010 |
| WO | WO 2010/033360 A1 | 3/2010 |
| WO | WO 2010/048207 A2 | 4/2010 |
| WO | WO 2010/060379 A1 | 6/2010 |
| WO | WO 2010/075376 A2 | 7/2010 |
| WO | WO 2010/129497 A1 | 11/2010 |
| WO | WO 2010/133336 A1 | 11/2010 |
| WO | WO 2010/146236 A1 | 12/2010 |
| WO | WO 2011/003065 A2 | 1/2011 |
| WO | WO 2011/043371 A1 | 4/2011 |
| WO | WO 2011/045224 A1 | 4/2011 |
| WO | WO 2011/045240 A1 | 4/2011 |
| WO | WO 2011/091153 A1 | 7/2011 |
| WO | WO 2011/101229 A1 | 8/2011 |
| WO | WO 2011/126903 A2 | 10/2011 |
| WO | WO 2011/128304 A1 | 10/2011 |
| WO | WO 2011/134964 A1 | 11/2011 |
| WO | WO 2011/138285 A1 | 11/2011 |
| WO | WO 2011/163518 A1 | 12/2011 |
| WO | WO 2012/000896 A2 | 1/2012 |
| WO | WO 2012/004217 A1 | 1/2012 |
| WO | WO 2012/007500 A2 | 1/2012 |
| WO | WO 2012/035011 A1 | 3/2012 |
| WO | WO 2012/052412 A1 | 4/2012 |
| WO | WO 2012/061290 A2 | 5/2012 |
| WO | WO 2012/070114 A1 | 5/2012 |
| WO | WO 2012/102387 A1 | 8/2012 |
| WO | WO 2012/108511 A1 | 8/2012 |
| WO | WO 2012/147107 A2 | 11/2012 |
| WO | WO 2012/168361 A1 | 12/2012 |
| WO | WO 2013/000931 A1 | 1/2013 |
| WO | WO 2013/010946 A2 | 1/2013 |
| WO | WO 2013/010947 A2 | 1/2013 |
| WO | WO 2013/062980 A1 | 5/2013 |
| WO | WO 2013/064324 A1 | 5/2013 |
| WO | WO 2013/156431 A1 | 10/2013 |
| WO | WO 2013/156433 A1 | 10/2013 |

OTHER PUBLICATIONS

International Search Report and Written Opinion for PCT/US2014/061007 mailed Dec. 31, 2014.
International Search Report and Written Opinion for PCT/US2014/061009 mailed Dec. 8, 2014.
International Search Report and Written Opinion for PCT/US2014/061010 mailed Dec. 15, 2014.
International Search Report and Written Opinion for PCT/US2014/061012 mailed Dec. 15, 2014.
International Search Report and Written Opinion for PCT/US2014/061014 mailed Dec. 15, 2014.
International Search Report and Written Opinion for PCT/US2014/061016 mailed Dec. 15, 2014.
International Search Report and Written Opinion for PCT/US2014/061022 mailed Dec. 29, 2014.
International Search Report and Written Opinion for PCT/US2014/061023 mailed Dec. 15, 2014.
International Search Report and Written Opinion for PCT/US2014/061024 mailed Dec. 15, 2014.
International Search Report and Written Opinion for PCT/US2014/061027 mailed Dec. 15, 2014.
International Search Report and Written Opinion for PCT/US2014/061029 mailed Dec. 15, 2014.
International Search Report and Written Opinion for PCT/US2014/061030 mailed Dec. 15, 2014.
International Preliminary Report on Patentability for PCT/US2011/058578 mailed Dec. 21, 2012.
International Search Report and Written Opinion for PCT/US2011/058578 mailed Apr. 5, 2012.
International Search Report and Written Opinion for PCT/US2013/029615 mailed May 8, 2013.

PROCESS FOR THE PREPARATION OF 3-(3-CHLORO-1H-PYRAZOL-1-YL)PYRIDINE

CROSS REFERENCE TO RELATED APPLICATIONS

This Application claims the benefit of the following U.S. Provisional Patent Applications: Ser. No. 62/031,547, filed Jul. 31, 2014, the entire disclosure of which is hereby expressly incorporated by reference into this Application.

BACKGROUND

The present invention concerns an improved process for preparing 3-(3-chloro-1H-pyrazol-1-yl)pyridine.

US 20130288893(A1) describes, inter alia, certain (3-halo-1-(pyridin-3-yl)-1H-pyrazol-4-yl)amides and carbamates and their use as pesticides. The route to prepare such compounds involved the preparation of 3-(3-chloro-1H-pyrazol-1-yl)pyridine (5b) by the direct coupling of 3-bromopyridine with 3-chloropyrazole. The 3-chloropyrazole was prepared by a) treating 1H-pyrazole with 2-dimethylsulfamoyl chloride and sodium hydride to provide N,N-dimethyl-1H-pyrazole-1-sulfonamide, b) treating the N,N-dimethyl-1H-pyrazole-1-sulfonamide with perchloroethane and n-butyl lithium to provide 3-chloro-N,N-dimethyl-1H-pyrazole-1-sulfonamide, and c) removing the N,N-dimethylsulfonamide from 3-chloro-N,N-dimethyl-1H-pyrazole-1-sulfonamide with trifluoroacetic acid to give the 3-chloropyrazole.

The disclosed process produces low yields, relies on a starting material that is difficult to prepare (3-chloropyrazole) and provides a product that is difficult to isolate in a pure form. It would be desirable to have a process for preparing 3-(3-chloro-1H-pyrazol-1-yl)pyridine that avoids these problems.

SUMMARY

The present invention provides such an alternative by cyclizing 3-hydrazinopyridine•dihydrochloride with acrylonitrile to provide 1-(pyridin-3-yl)-4,5-dihydro-1H-pyrazol-3-amine (9a), by oxidizing to provide 3-(3-amino-1H-pyrazol-1-yl)pyridine (8a), and by converting the amino group to a chloro group by a Sandmeyer reaction. Thus, the present invention concerns a process for preparing 3-(3-chloro-1H-pyrazol-1-yl)pyridine (5b),

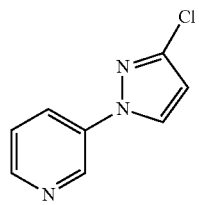
(5b)

which comprises a) treating 3-hydrazinopyridine•dihydrochloride

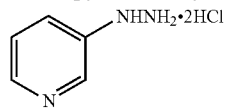

with acrylonitrile

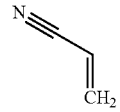

in a ($C_1$-$C_4$) aliphatic alcohol at a temperature of about 25° C. to about 100° C. in the presence of an alkali metal ($C_1$-$C_4$) alkoxide to provide 1-(pyridin-3-yl)-4,5-dihydro-1H-pyrazol-3-amine (9a)

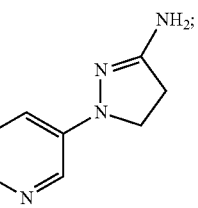
(9a)

b) treating the 1-(pyridin-3-yl)-4,5-dihydro-1H-pyrazol-3-amine (9a) with an oxidant in an inert organic solvent at a temperature of about 25° C. to about 100° C. to provide 3-(3-amino-1H-pyrazol-1-yl)pyridine (8a)

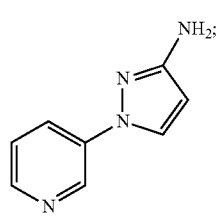
(8a)

c) treating the 3-(3-amino-1H-pyrazol-1-yl)pyridine (8a) in aqueous hydrochloric acid with sodium nitrite at a temperature of about 0° C. to about 25° C. to provide the diazonium salt (8b)

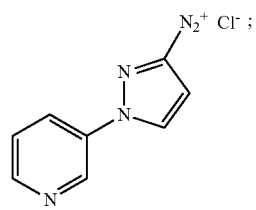
(8b)

and d) treating the diazonium salt (8b) with copper chloride at a temperature of about 0° C. to about 25° C.

DETAILED DESCRIPTION

The present invention provides an improved process for preparing 3-(3-chloro-1H-pyrazol-1-yl)pyridine (5b), by cyclizing 3-hydrazinopyridine•dihydrochloride with acrylonitrile to provide 1-(pyridin-3-yl)-4,5-dihydro-1H-pyrazol-3-amine (9a), by oxidizing to provide 3-(3-amino-1H-pyrazol-1-yl)pyridine (8a), and by converting the amino group to a chloro group by a Sandmeyer reaction.

In the first step, 3-hydrazinopyridine•dihydrochloride is treated with acrylonitrile in a ($C_1$-$C_4$) aliphatic alcohol at a temperature of about 25° C. to about 100° C. in the presence of an alkali metal ($C_1$-$C_4$) alkoxide to provide 1-(pyridin-3-yl)-4,5-dihydro-1H-pyrazol-3-amine. While stoichiometric amounts of 3-hydrazinopyridine•dihydrochloride and acrylonitrile are required, it is often convenient to use about a 1.5 fold to about a 2 fold excess of acrylonitrile. The cyclization is run in the presence of an alkali metal ($C_1$-$C_4$) alkoxide base. It is often convenient to use about a 2 fold to about a 5 fold excess of base. The cyclization is performed in a ($C_1$-$C_4$) aliphatic alcohol. It is most convenient that the alkoxide base and the alcohol solvent be the same, for example, sodium ethoxide in ethanol.

In a typical reaction, 3-hydrazinopyridine•dihydrochloride and an anhydrous alcohol are introduced into a reaction vessel and the alkoxide base is gradually added. The mixture is stirred and the acrylonitrile is added. The mixture is stirred at about 60° C. until most of the 3-hydrazinopyridine has reacted. The mixture is allowed to cool and the excess base is neutralized with acid. The crude 1-(pyridin-3-yl)-4,5-dihydro-1H-pyrazol-3-amine (9a) is conveniently isolated and purified by standard techniques.

In the second step, 1-(pyridin-3-yl)-4,5-dihydro-1H-pyrazol-3-amine (9a) is treated with an oxidant in an organic solvent at a temperature of about 25° C. to about 100° C. to provide 3-(3-amino-1H-pyrazol-1-yl)pyridine (8a). Suitable oxidants include manganese(IV) oxide, potassium ferricyanide(III), copper(I) chloride in the presence of oxygen, and iron(III) chloride in the presence of oxygen. Manganese(IV) oxide is preferred. It is often convenient to use about a 2 fold to about a 10 fold excess of oxidant. The oxidation is performed in a solvent that is inert to the oxidant. Suitable solvents include nitriles such as acetonitrile or halocarbons such as dichloromethane. With manganese(IV) oxide as the oxidant, acetonitrile is a preferred solvent.

In a typical reaction, 1-(pyridin-3-yl)-4,5-dihydro-1H-pyrazol-3-amine (9a) and solvent are mixed with the oxidant and the mixture is heated at about 60° C. until the reaction is completed. The 3-(3-amino-1H-pyrazol-1-yl)pyridine (8a) is conveniently isolated and purified by standard techniques.

The 3-(3-amino-1H-pyrazol-1-yl)pyridine (8a) is then converted to the desired 3-(3-chloro-1H-pyrazol-1-yl)pyridine (5b) by treatment in aqueous hydrochloric acid with sodium nitrite at a temperature of about 0° C. to about 25° C. to provide a diazonium salt followed by treatment of the diazonium salt with copper chloride at a temperature of about 0° C. to about 25° C. While stoichiometric amounts of reagents are required, it is often convenient to use an excesses of reagents with respect to the 3-(3-amino-1H-pyrazol-1-yl)pyridine (8a). Thus, aqueous hydrochloric acid is used in large excess as the reaction medium. Sodium nitrite is used in about a 1.3 fold to about a 2 fold excess. Copper chloride is used in about 5 mole percent to about 60 mole percent excess, preferably from about 15 mole percent to about 30 mole percent excess. The copper chloride may be either copper(I) chloride or copper(II) chloride. To suppress foaming during the reaction a water-immiscible organic solvent such as toluene or chloroform can be added during the treatment of the diazonium salt with copper chloride.

In a typical reaction, a mixture of 3-(3-amino-1H-pyrazol-1-yl)pyridine (8a) and aqueous hydrochloric acid are mixed and cooled to about 0° C. An aqueous solution of sodium nitrite is slowly added maintaining the temperature below about 5° C. The suspension is stirred at about 0° C. for about 2 hours. In a separate vessel, a mixture of copper(II) chloride and toluene is cooled to about 0° C. and the chilled suspension of diazonium salt is added at a rate maintaining the temperature below about 5° C. The mixture is allowed to warm to about ambient temperature. After completion of the reaction, the mixture is treated with aqueous sodium hydroxide to adjust the pH to about 8 to about 10. The resulting solution is extracted with a water-immiscible organic solvent. After removal of the solvent, the 3-(3-chloro-1H-pyrazol-1-yl)pyridine (5b) can be used directly in the next reaction or further purified by standard techniques such as flash column chromatography or crystallization.

The following examples are presented to illustrate the invention.

EXAMPLES

1. Preparation of 1-(pyridin-3-yl)-4,5-dihydro-1H-pyrazol-3-amine (9a)

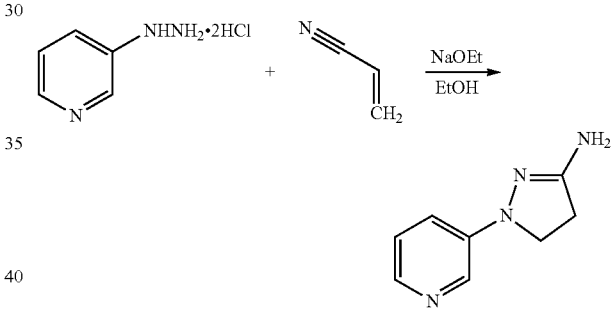

To a 4-neck, round bottomed flask (250 mL) was charged sodium ethanolate (21 wt % in ethanol, 32 mL). 3-Hydrazinopyridine•dihydrochloride (5.00 g, 27.5 mmol) was added, causing an exotherm from 20° C. to 58° C. The mixture was allowed to cool to 20° C. and acrylonitrile (2.91 g, 54.9 mmol) was added. The reaction was heated at 60° C. for 5 hours and cooled to 20° C. The excess sodium ethanolate was quenched with hydrochloric acid (4 M in 1,4-dioxane, 6.88 mL, 27.5 mmol) at <20° C. The mixture was adsorbed on silica gel (10 g) and the crude product was purified by flash column chromatography using 0-10% methanol/dichloromethane as eluent. The fractions containing pure product were concentrated to dryness to afford the title compound as a yellow solid (3.28 g, 74%): mp 156-160° C.; $^1$H NMR (400 MHz, CDCl$_3$) δ 8.24 (dd, J=2.8, 0.8 Hz, 1H), 8.01 (dd, J=4.6, 1.4 Hz, 1H), 7.22 (ddd, J=8.4, 2.8, 1.5 Hz, 1H), 7.12 (ddd, J=8.4, 4.6, 0.8 Hz, 1H), 4.20 (s, 2H), 3.70 (t, J=9.3 Hz, 2H), 2.92 (t, J=9.3 Hz, 2H); $^{13}$C NMR (101 MHz, CDCl$_3$) δ 154.23, 144.78, 139.22, 135.08, 123.44, 119.44, 49.23, 32.74; ESIMS m/z 163 ([M+H]$^+$).

2. Preparation of 3-(3-amino-1H-pyrazol-1-yl)pyridine (8a)

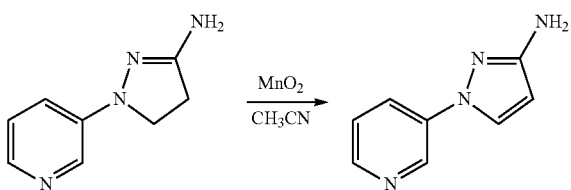

To a 3-neck, round bottomed flask (100 mL) was charged 1-(pyridin-3-yl)-4,5-dihydro-1H-pyrazol-3-amine (1.00 g, 6.17 mmol) and acetonitrile (20 mL). Manganese(IV) oxide (2.68 g, 30.8 mmol) was added, causing an exotherm from 20° C. to 25° C. The reaction was stirred at 60° C. for 18 hours, after which it was filtered through a Celite® pad and the pad was rinsed with acetonitrile (20 mL). Water (20 mL) was added to the combined filtrates and the resulting mixture was concentrated to 10 mL. Water (20 mL) was added and the resulting mixture was again concentrated to 10 mL. The resulting suspension was stirred at 20° C. for 18 hours and filtered. The filter cake was rinsed with water (2×5 mL) and dried to afford the title compound as a brown solid (0.68 g, 69%): mp 169-172° C.; $^1$H NMR (400 MHz, DMSO-$d_6$) δ 9.07-8.82 (m, 1H), 8.33 (dd, J=4.6, 1.5 Hz, 1H), 8.24 (d, J=2.6 Hz, 1H), 8.00 (ddd, J=8.4, 2.7, 1.4 Hz, 1H), 7.42 (ddd, J=8.5, 4.6, 0.8 Hz, 1H), 5.80 (d, J=2.6 Hz, 1H), 5.21 (s, 2H); $^{13}$C NMR (101 MHz, DMSO-$d_6$) δ 157.67, 144.68, 138.00, 136.22, 128.30, 123.95, 123.17, 97.08; ESIMS m/z 161 ([M+H]$^+$).

3. Preparation of 3-(3-chloro-1H-pyrazol-1-yl)pyridine (5b)

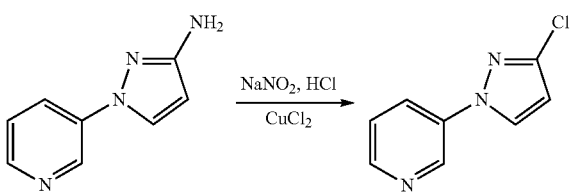

To a 3-neck round bottomed flask (250 mL) was charged 3-(3-amino-1H-pyrazol-1-yl)pyridine (5.00 g, 31.2 mmol) and hydrogen chloride (37 wt %, 15 mL). The mixture was cooled to 0° C. A solution of sodium nitrite (4.31 g, 62.4 mmol) in water (15 mL) was added in portions at <1° C. over 20 minutes and the resulting brown solution was stirred at <0° C. for 2 hours. To a separate 3-neck round bottomed flask (250 mL) was charged copper(II) chloride (5.04 g, 37.5 mmol) and toluene (30 mL). It was cooled to 0° C. and the yellow solution was added in portions at <1° C. over 15 minutes. The resulting mixture was allowed to warm up, off-gassing was observed when the reaction temperature reached 18° C. The reaction was stirred at 20° C. for 18 hours. The reaction was basified with 50 wt % sodium hydroxide to pH ~10. Celite® (10 g) was added and the resulting suspension was stirred for 10 minutes. The suspension was filtered through a Celite® pad (10 g) and the filter cake was rinsed with ethyl acetate (2×50 mL). The layers of the filtrates were separated and the aqueous layer was extracted with ethyl acetate (100 mL). The organic layers were concentrated to dryness and the residue was purified by flash column chromatography using 0-60% ethyl acetate/hexanes as eluent. The fractions containing the desired product were concentrated to give the title compound as a white solid (3.80 g, 68%): mp 104-106° C.; $^1$H NMR (400 MHz, CDCl$_3$) δ 8.93 (d, J=2.7 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (M, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.08; EIMS m/z 179 ([M]$^+$).

What is claimed is:
1. A process for preparing 3-(3-chloro-1H-pyrazol-1-yl)pyridine (5b),

(5b)

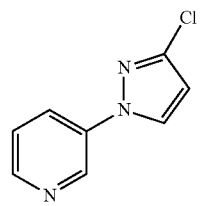

which comprises
a) treating 3-hydrazinopyridine·dihydrochloride

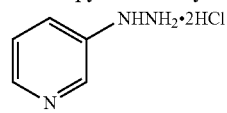

with acrylonitrile

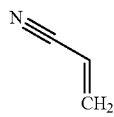

in a ($C_1$-$C_4$) aliphatic alcohol at a temperature of about 25° C. to about 100° C. in the presence of an alkali metal ($C_1$-$C_4$) alkoxide to provide 1-(pyridin-3-yl)-4,5-dihydro-1H-pyrazol-3-amine (9a)

(9a)

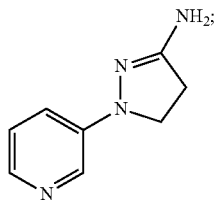

b) treating the 1-(pyridin-3-yl)-4,5-dihydro-1H-pyrazol-3-amine (9a) with an oxidant in an organic solvent at a temperature of about 25° C. to about 100° C. to provide 3-(3-amino-1H-pyrazol-1-yl)pyridine (8a)

(8a)

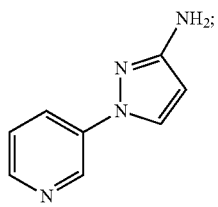

c) treating the 3-(3-amino-1H-pyrazol-1-yl)pyridine (8a) in aqueous hydrochloric acid with sodium nitrite at a temperature of about 0° C. to about 25° C. to provide the diazonium salt (8b)

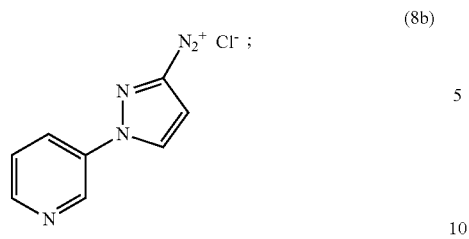

(8b)

and
    d) treating the diazonium salt (8b) with copper chloride at a temperature of about 0° C. to about 25° C.

2. The process of claim 1 in which the oxidant is manganese(IV) oxide, potassium ferricyanide (III), copper(I) chloride in the presence of oxygen, or iron(III) chloride in the presence of oxygen.

3. The process of claim 2 in which the oxidant is manganese(IV) oxide.

4. The process of claim 1 in which a water immiscible organic solvent is added in step d) to suppress foaming.

\* \* \* \* \*